(12) United States Patent
Chang et al.

(10) Patent No.: US 9,625,374 B2
(45) Date of Patent: Apr. 18, 2017

(54) IMAGE FORMING APPARATUS HAVING OPTICAL SENSOR SYSTEM, OPTICAL SENSOR SYSTEM HAVING SHIELDS, AND METHOD THEREOF

(75) Inventors: Seongsik Chang, Santa Clara, CA (US); Henryk Birecki, Palo Alto, CA (US); Krzysztof Nauka, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1198 days.

(21) Appl. No.: 13/238,281

(22) Filed: Sep. 21, 2011

(65) Prior Publication Data

US 2013/0070233 A1   Mar. 21, 2013

(51) Int. Cl.
*G01N 21/3504* (2014.01)
*G01N 21/15* (2006.01)

(52) U.S. Cl.
CPC ......... *G01N 21/3504* (2013.01); *G01N 21/15* (2013.01); *G01N 2021/151* (2013.01); *G01N 2021/3513* (2013.01)

(58) Field of Classification Search
CPC .............................................. G01N 21/3504
USPC ........................................................ 356/72
See application file for complete search history.

(56) References Cited

U.S. PATENT DOCUMENTS

| | | | |
|---|---|---|---|
| 5,790,246 A * | 8/1998 | Kuhnell et al. | 356/72 |
| 7,708,947 B2 | 5/2010 | West et al. | |
| 7,924,412 B2 * | 4/2011 | Chopra et al. | 356/72 |
| 7,972,865 B2 | 7/2011 | Yi et al. | |
| 2010/0110437 A1 * | 5/2010 | Furtaw et al. | 356/437 |
| 2011/0048106 A1 | 3/2011 | Zawacki et al. | |

OTHER PUBLICATIONS

"What Precautions Should I Take When Using the Hobo Pro Data Loggers Outside?", <http://www.onsetcomp.com/support/faq/what-precautions-should-i-take-when-using-hobo-pro-loggers-outside>, 2011.

Stewart, K.M.E; "Doped Polyaniline for Gas Sensors for the Detection of Formaldehyde", <http://uwspace.uwaterloo.ca/bitstream/10012/5852/1/Stewart_Katherine.pdf>, 2011.

Stockdale, Mark; "Minipid User Manual V1.8", <http://www.ionscience.com/assets/files/manuals/MiniPID%20Manual%203%20Pin%20V1.8.pdf>, Aug. 11, 2010.

* cited by examiner

*Primary Examiner* — Tarifur Chowdhury
*Assistant Examiner* — Omar Nixon
(74) *Attorney, Agent, or Firm* — HP Inc. Patent Department

(57) ABSTRACT

An optical sensor system includes a source module and a detection module. The source module includes a source housing unit having a source window member and a source shielding member. The source module emits a detection signal through the source window member. The detection module includes a detection housing unit having a detection window member and a detection shielding member. The detection module is spaced apart from the source module. The detection module detects the detection signal emitted from the source module at the detection window member.

20 Claims, 6 Drawing Sheets

IMAGE FORMING APPARATUS HAVING OPTICAL SENSOR SYSTEM, OPTICAL SENSOR SYSTEM HAVING SHIELDS, AND METHOD THEREOF

CROSS REFERENCE TO RELATED APPLICATIONS

This application is related to commonly-owned patent application Ser. No. 13/238,015, entitled "IMAGE FORMING APPARATUS HAVING OPTICAL SENSOR SYSTEM, OPTICAL SENSOR SYSTEM HAVING DETECTION MODULES, AND METHOD THEREOF" and filed contemporaneously herewith by Henryk Birecki, Krzysztof Nauka, and Seongsik Chang, and Ser. No. 13/238,001, entitled "IMAGE FORMING APPARATUS HAVING OPTICAL SENSOR SYSTEM, OPTICAL SENSOR SYSTEM HAVING HEATING MODULE, AND METHOD THEREOF" and filed contemporaneously herewith by Krzysztof Nauka, Seongsik Chang, and Henryk Birecki, and which related applications are incorporated herein by reference in their entirety.

BACKGROUND

Optical sensor systems may include source modules and detection modules to detect the presence of objects there between. The source modules may include a source window member to emit a detection signal such as an infrared signal there through to be received by a detection module through a detection window member thereof. The objects such as volatile organic compounds (VOC) may be detected present in a path of the detection signal. Such optical sensor systems may be included in image forming apparatuses, air quality monitoring devices, or the like.

BRIEF DESCRIPTION OF THE DRAWINGS

Non-limiting examples of the present disclosure are described in the following description, read with reference to the figures attached hereto and do not limit the scope of the claims. In the figures, identical and similar structures, elements or parts thereof that appear in more than one figure are generally labeled with the same or similar references in the figures in which they appear. Dimensions of components and features illustrated in the figures are chosen primarily for convenience and clarity of presentation and are not necessarily to scale. Referring to the attached figures:

DETAILED DESCRIPTION

Figure 1:
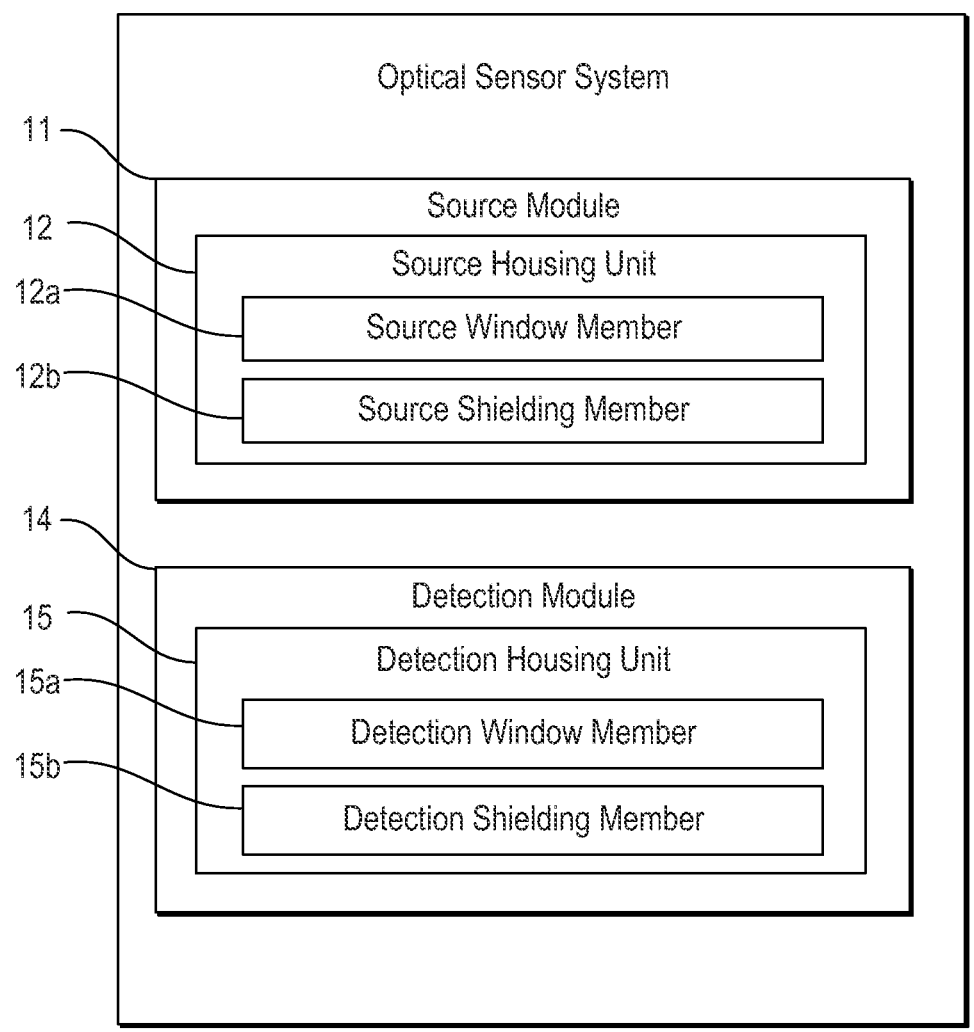
FIG. 1 is a block diagram illustrating an optical sensor system according to an example.

In the following detailed description, reference is made to the accompanying drawings which form a part hereof, and in which is depicted by way of illustration specific examples in which the present disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims.

Optical sensor systems may include source modules and detection modules to detect the presence of objects there between such as volatile organic compounds (VOC). For example, VOC may be in a form of a gas, liquid and/or solid and include organic compounds that may easily become vapor or gaseous. An optical sensor system may detect VOC in a form of a gas in a volume of air between a source module and a detection module, for example, to be used as a basis for determining a total amount of VOC in a form of a gas present in an environment. Such information may be used to provide alerts based on VOC concentration and/or activate processes to reduce VOC concentration. The source modules may include a source window member to emit a detection signal such as an infrared signal there through to be received by a detection module through a detection window member thereof. The objects, for example, such as VOC may be detected when present in path of the detection signal. Such optical sensor systems may be included in image forming apparatuses, air quality monitoring devices, or the like. The image forming apparatuses may include liquid electrophotography printing apparatuses to form images on an image transfer blanket that, subsequently, get transferred to media. Unwanted deposits in a form of solid and/or liquid buildup such as VOC deposits, however, may form on the source window member and the detection window member. The deposits may decrease transmission of the detection signal through the respective window members, for example, by absorbing some frequencies of the detection signal and/or promoting scattering due to non-uniformity of the thickness of the deposits. Consequently, the detection signal may be degraded and/or potentially distort detection of objects such as the VOC in a form of gas present in the path of the detection signal resulting in incorrect VOC reading by the detection module.

In examples, an optical sensor system includes, amongst other things, a source module including a source housing unit and a detection module including a detection housing unit. The source housing unit includes a source window member and a source shielding member. The source module emits a detection signal through the source window member. The detection housing unit includes a detection window member and a detection shielding member. The detection module detects the detection signal emitted from the source module thereto. The source shielding member surrounds the source window member and extends in an outward direction from the source window member. The detection shielding member surrounds the detection window member and extends in an outward direction from the detection window member. The shielding members may reduce and/or delay deposit formation of VOC on the corresponding window members that the respective shielding members surround. Thus, degradation of the detection signal and/or potentially distortion of the detection of objects such as the VOC in the form of gas present in the path of the detection signal due to deposit formation on respective window members may be reduced.

FIG. 1 is a block diagram illustrating an optical sensor system according to an example. Referring to FIG. 1, in some examples, an optical sensor system 100 includes a source module 11 and a detection module 14. The source module 11 includes a source housing unit 12 having a source window member 12a and a source shielding member 12b. The source shielding member 12b surrounds the source window member 12a and extends in an outward direction $d_{so}$ (FIGS. 2A and 2B) from the source window member 12a. The source module 11 may emit a detection signal through the source window member 12a. The detection module 14 is spaced apart from the source module 11. The detection module 14 includes a detection housing unit 15 having a detection window member 15a and a detection shielding member 15b. The detection shielding member 15b surrounds the detection window member 15a and extends in an outward direction $d_{do}$ from the detection window member 15a.

Figure 2A:
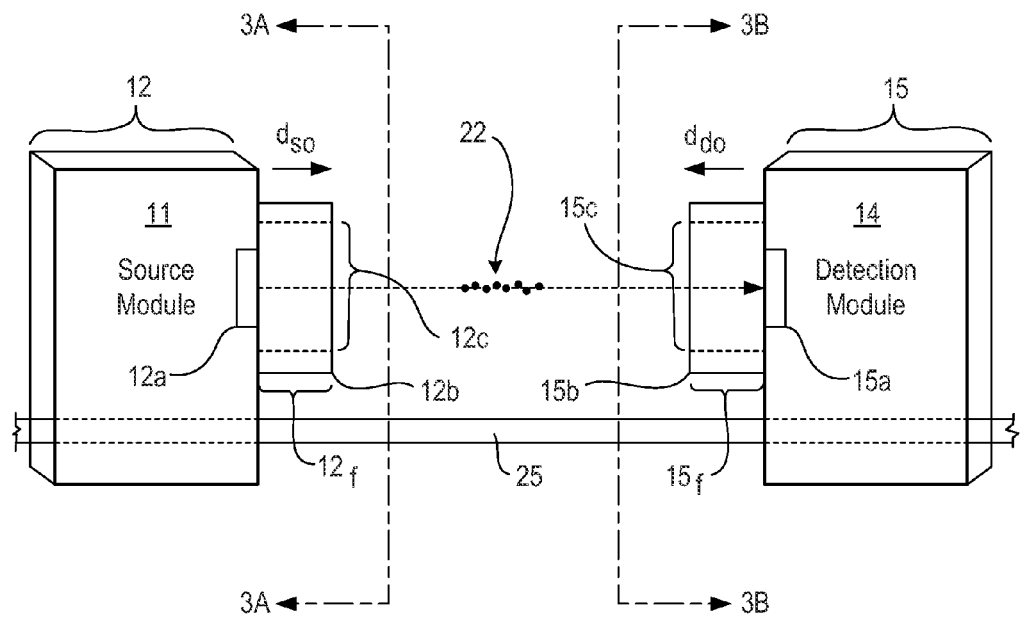
FIG. 2A is a side view illustrating the optical sensor system of FIG. 1 according to an example.
Figure 2B:
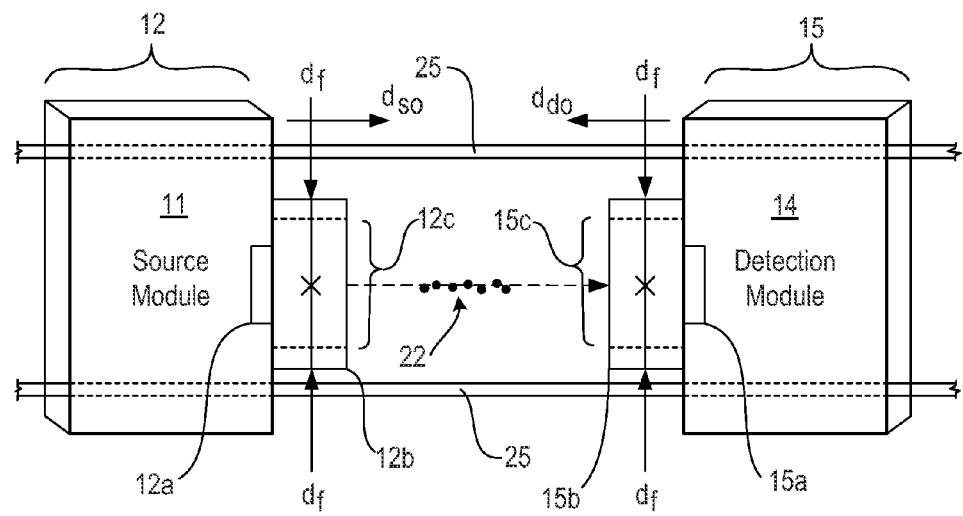
FIG. 2B is a top view of the optical sensor system of FIG. 2A according to an example.
Figure 3A:
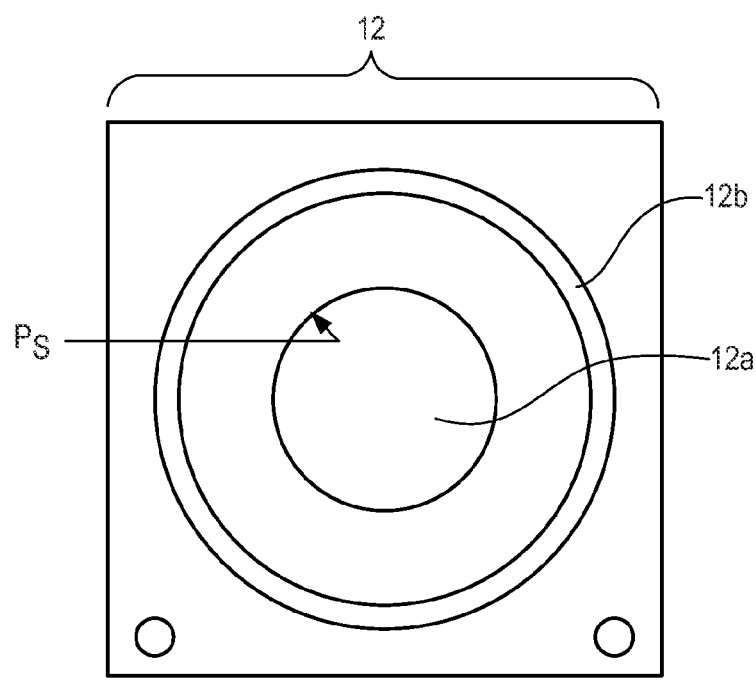
FIGS. 3A and 3C are front views of a source module of the optical sensor system of FIG. 2A according to examples.
Figure 3B:
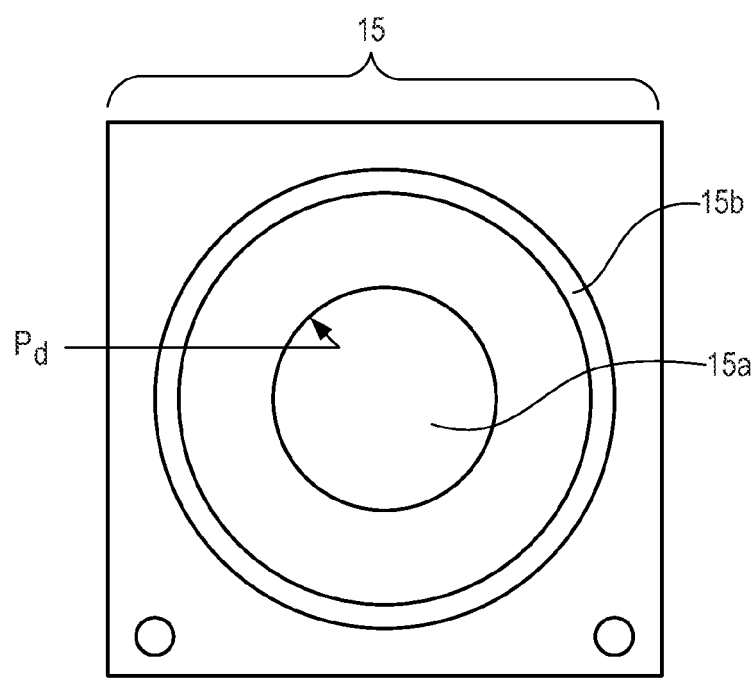
FIGS. 3B and 3D are front views of a detection module of the optical sensor system of FIG. 2A according to examples.
Figure 3C:
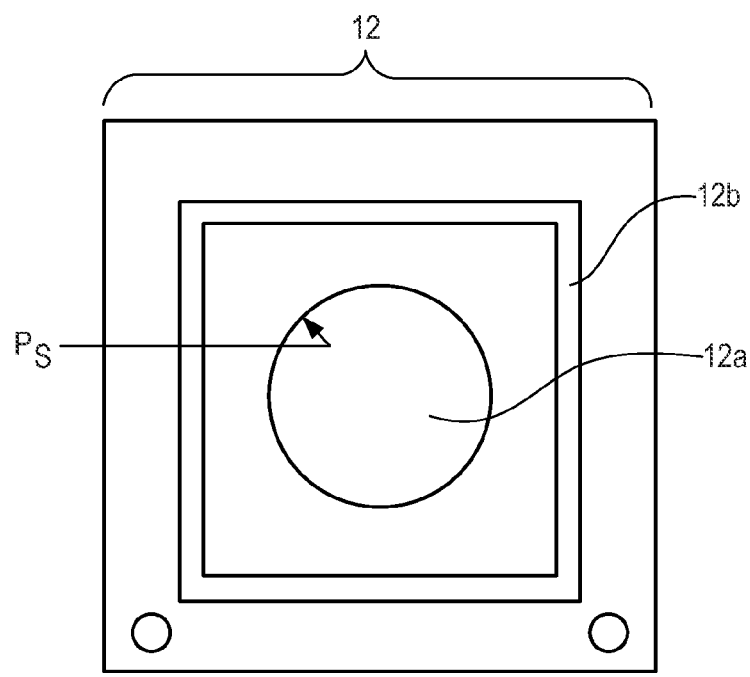
Figure 3D:
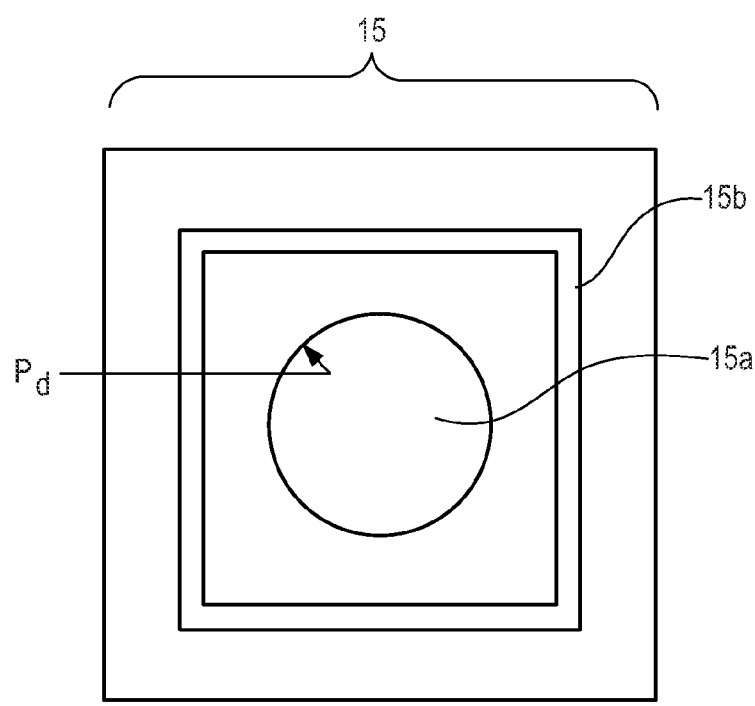

FIG. 2A is a side view illustrating the optical sensor system of FIG. 1 according to an example. FIG. 2B is a top view illustrating the optical sensor system of FIG. 2A according to an example. FIGS. 3A and 3C are front views of a source module of the optical sensor system of FIG. 2A according to examples. FIGS. 3B and 3D are front views of a detection module of the optical sensor system of FIG. 2A according to examples. Referring to FIGS. 2A-3D, in some examples, the source window member 12a includes a source perimeter $p_s$ and the detection window member 15a includes a detection perimeter $p_d$, for example, generally perpendicular to a direction of the detection signal emitted from the source module 11. In some examples, the source shielding member 12b may surround the entire source perimeter $p_s$ of the source window member 12a perpendicular to a direction of the detection signal emitted by the source module 11. Additionally, the detection shielding member 15b may surround the entire perimeter $p_d$ of the detection window member 15a perpendicular to the direction of the detection signal emitted by the source module 11. Perimeters $p_s$ and $p_d$ may be selected to minimize an amount of signal that the respective shielding members 12b and 15b may intersect. For example, the perimeters $p_s$ and $p_d$ may be at least of a size of the source module window member 12a and the detection module window member 15a, respectively. Elongated bodies 12f and 15f of the source shielding member 12b and the detection shielding member 15b may include an outer surface surrounding the source perimeter $p_s$ and the detection perimeter $d_s$, respectively, having a variety of shapes including a rectangular shape and a circular shape.

Referring to FIGS. 2A-3D, in some examples, each one of the source shielding member 12b and the detection shielding member 15b may include an elongated body 12f and 15f. The respective elongated bodies 12f and 15f may include a longitudinal opening 12c and 15c extending therein. That is, the longitudinal opening 12c may extend throughout the elongated body 12f of the respective shielding member 12b to allow the detection signal to pass there through. For example, a cross-sectional area of the longitudinal opening 12c and 15c of the elongated body 12f and 15f of each of the source shielding member 12b and the detection shielding member 15 perpendicular to a direction of the detection signal emitted by the source module 11 are greater than a cross-sectional area of the source window member 12a and the detection window member 15a. Thus, the detection signal may pass there through without the respective shielding members 12b and 15b obstructing and/or degrading the detection signal.

Referring to FIGS. 2A-3D, in some examples, the detection module 14 may detect VOC 22 present in the path of the detection signal between the source module 11 and the detection module 14. Thus, the source shielding member 12b may reduce deposit formation of the VOC on the source window member 12a and the detection shielding member 15b may reduce deposit formation of the VOC on the detection window member 15a. For example, the elongated body 12f and 15f of the source shielding member 12b and the detection shielding member 15b may be disposed traverse to a direction of air flow $d_f$ transporting the VOC 22. For example, air flow may be created by exhaust fans, fans providing air circulation external and proximate to the optical sensor system 100 such as devices including the optical sensor system 100, hot air convection external and proximate to the optical sensor system 100 such as devices including the optical sensor system 100, or the like. Thus, the respective elongated bodies 12f and 15f may block the air flow from directly contacting the source window member 12a and the detection window member 15a, respectively, in an uninterrupted manner. That is, the respective elongated bodies 12f and 15f reduce the number of direct paths for the VOC to contact the source window member 12a and the detection window member 15a.

Referring to FIGS. 2A-3D, in some examples, the optical sensor system 100 may include at least one guide member 25 to guide the source housing unit 12 and the detection housing unit 15 toward and away from each other to adjust a distance there between. For example, the optical sensor system 100 may include a pair of guide members 25 disposed through each of the source housing unit 12 and the detection housing unit 15 to allow the respective housing members 12a and 15a to slide toward and away from each other along the guide members 25. Alternatively, the optical sensor system 100 may include a solid member connecting the source housing unit 12 and the detection housing unit 15 to provide a rigid structure and permanent alignment for the source module 11, detection module 14, and parts thereof.

In some examples, the source module 11 and/or the detection module 14 may be implemented in hardware, or in a combination of hardware and software. In some examples, the source module 11 and the detection module 14 may be implemented in part as a computer program such as a set of machine-readable instructions stored in the optical sensor system 100 locally or remotely. For example, the computer program may be stored in a memory such as a server or a host computing device considered herein as part of the optical sensor system 100.

Figure 4:
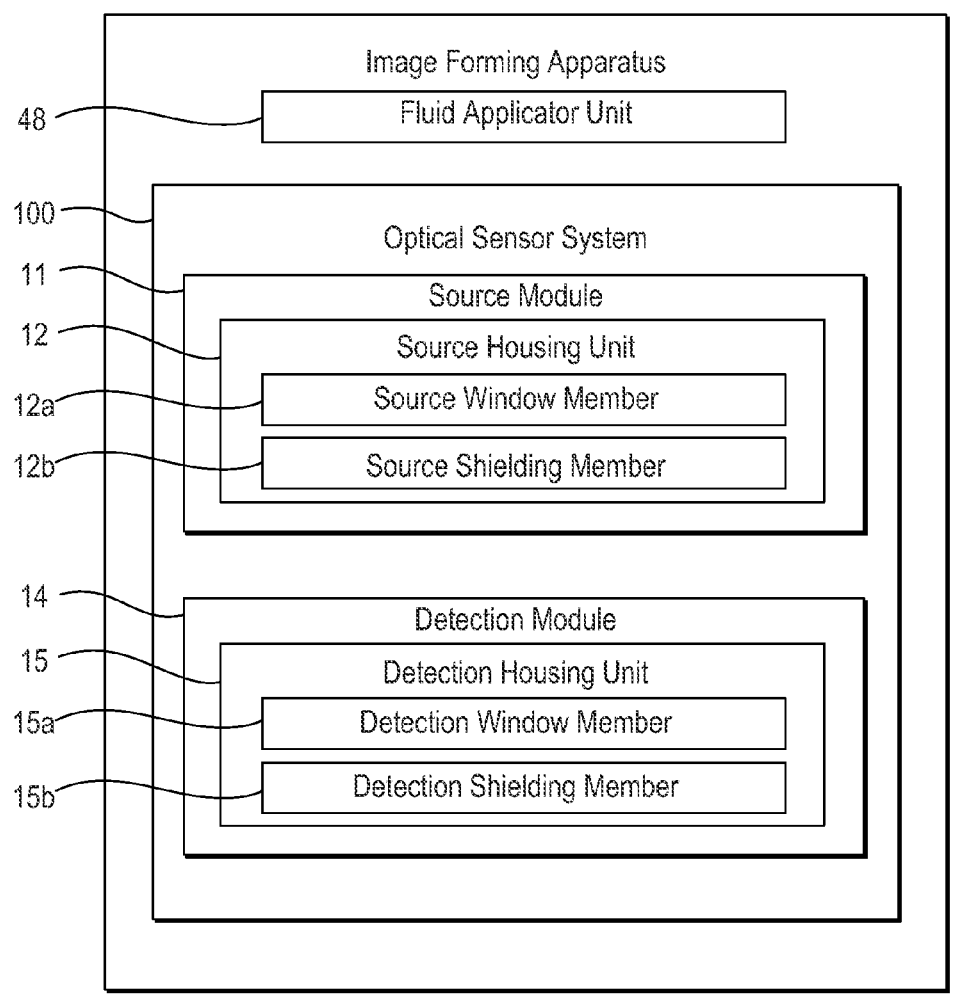
FIG. 4 is a block diagram illustrating an image forming apparatus having an optical sensor system according to an example.

FIG. 4 is a block diagram illustrating an image forming apparatus including an optical sensor system according to an example. In some examples, the image forming apparatus 400 may include a liquid electrophotograpy printing apparatus that forms images on media by applying fluid onto an intermediate transfer member and, subsequently, onto the media. For example, the fluid may include ink such as liquid toner, for example, ElectroInk, trademarked by Hewlett-Packard Company including imaging oil. The imaging oil may include low weight liquid aliphatic hydrocarbons, for example, Isopar, trademarked by Exxon Corporation. Referring to FIG. 4, in some examples, an image forming apparatus 400 includes a fluid applicator unit 48 and an optical sensor system 100. The fluid applicator unit 48 may apply fluid to an object to form an image. For example, the fluid applicator unit 48 may include an inkjet print head, a binary developer unit, or the like. In some examples, the image forming apparatus 400 may include the optical sensor system 100 as previously disclosed with respect to FIGS. 1-3D.

Referring to FIG. 4, in some examples, the optical sensor system 100 may detect VOC formed from the fluid applied by the fluid applicator unit 48. The optical sensor system 100 may include a source module 11 and a detection module 14 spaced apart from each other. For example, the source module 11 may include a source housing unit 12 having a source window member 12a and a source shielding member 12b. The source module 11 may emit a detection signal through the source window member 12a to detect the VOC present in the path of a detection signal between the source module 11 and the detection module 14. The source shielding member 12b may surround and extend in an outward direction $d_{so}$ from the source window member 12a to reduce deposit formation of the VOC on the source window member 12a.

Referring to FIG. 4, in some examples, the detection module 14 may include a detection housing unit 15 having a detection window member 15a and a detection shielding member 15b to receive the detection signal emitted from the source module 11 at the detection window member 15a. The detection shielding member 15b may surround and extend in an outward direction $d_{do}$ from the detection window member 15a to reduce deposit formation of the VOC on the detection window member 15a. For example, the elongated body 12f and 15f of the source shielding member 12b and the detection shielding member 15b are disposed traverse to a direction of air flow $d_f$ transporting the VOC to block the air flow from directly contacting the source window member 12a and the detection window member 15a, respectively, in an uninterrupted manner.

Figure 5:
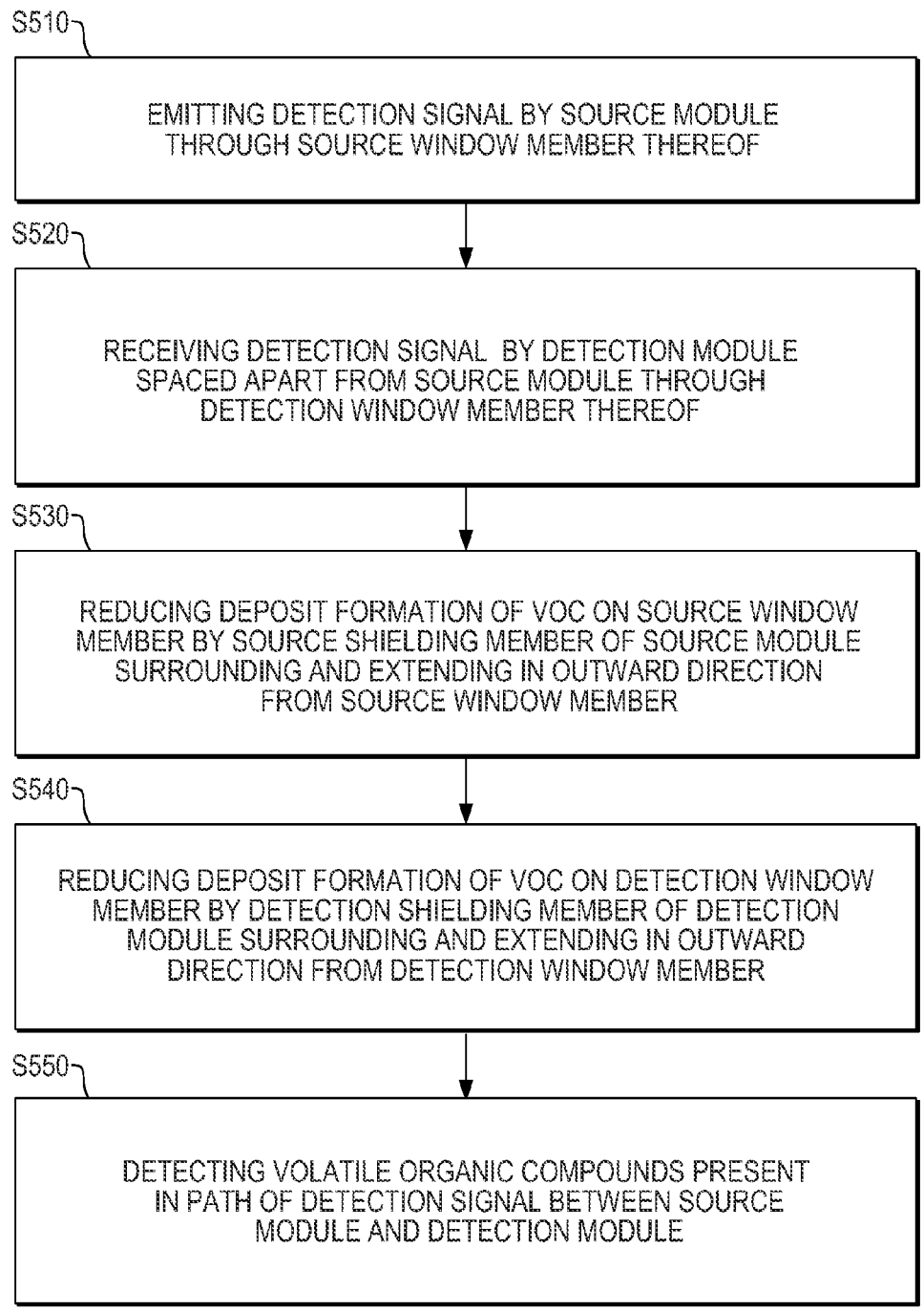
FIG. 5 is a flowchart illustrating a method of detecting volatile organic compounds according to an example.

FIG. 5 is a flowchart illustrating a method of detecting volatile organic compounds according to an example. Referring to FIG. 5, in block S510, a detection signal is emitted by a source module through a source window member thereof. In block S520, the detection signal is received by a detection module spaced apart from the source module through a detection window member thereof. In block S530, deposit formation of VOC on the source window member is reduced by a source shielding member of the source module surrounding and extending in an outward direction from the source window member. The reducing of deposit formation of the VOC on the source window member may also include blocking air flow transporting the VOC from directly contacting the source window member in an uninterrupted manner by an elongated body of the source shielding member disposed traverse to a direction of the air flow. In block S540, deposit formation of the VOC on the detection window member is reduced by a detection shielding member of the detection module surrounding and extending in an outward direction from the detection window member. The reducing deposit formation of the VOC on the detection window member may also include blocking air flow transporting the VOC from directly contacting the detection window member in an uninterrupted manner by an elongated body of the detection shielding member disposed traverse to a direction of the air flow. In block S550, the volatile organic compounds present in a path of the detection signal between the source module and the detection module are detected.

It is to be understood that the flowchart of FIG. 5 illustrates an architecture, functionality, and operation of an example of the present disclosure. If embodied in software, each block may represent a module, segment, or portion of code that includes one or more executable instructions to implement the specified logical function(s). If embodied in hardware, each block may represent a circuit or a number of interconnected circuits to implement the specified logical function(s). Although the flowchart of FIG. 5 illustrates a specific order of execution, the order of execution may differ from that which is depicted. For example, the order of execution of two or more blocks may be scrambled relative to the order illustrated. Also, two or more blocks illustrated in succession in FIG. 5 may be executed concurrently or with partial concurrence. All such variations are within the scope of the present disclosure.

The present disclosure has been described using non-limiting detailed descriptions of examples thereof and is not intended to limit the scope of the present disclosure. It should be understood that features and/or operations described with respect to one example may be used with other examples and that not all examples of the present disclosure have all of the features and/or operations illustrated in a particular figure or described with respect to one of the examples. Variations of examples described will occur to persons of the art. Furthermore, the terms "comprise," "include," "have" and their conjugates, shall mean, when used in the present disclosure and/or claims, "including but not necessarily limited to."

It is noted that some of the above described examples may include structure, acts or details of structures and acts that may not be essential to the present disclosure and are intended to be exemplary. Structure and acts described herein are replaceable by equivalents, which perform the same function, even if the structure or acts are different, as known in the art. Therefore, the scope of the present disclosure is limited only by the elements and limitations as used in the claims.

What is claimed is:

1. An optical sensor system, comprising:
a source module including a source housing unit having a source window member and a source shielding member, the source module to emit a detection signal through the source window member;
the source shielding member surrounding the source window member and extending in an outward direction from the source window member; and
a detection module including a detection housing unit having a detection window member and a detection shielding member, the detection module to detect the detection signal emitted from the source module at the detection window member and spaced apart from the source module;
the detection shielding member surrounding the detection window member and extending in an outward direction from the detection window member;
wherein distal ends of the source shielding member and the detection shielding member are spaced from and opposed to each other.

2. The optical sensor system according to claim 1, further comprising:
at least one guide member to guide the source housing unit and the detection housing unit toward and away from each other to adjust a distance there between.

3. The optical sensor system according to claim 1, wherein the source shielding member is a unitary member and surrounds an entire perimeter of the source window member perpendicular to a direction of the detection signal emitted by the source module and the detection shielding member is a unitary member and surrounds an entire perimeter of the detection window member perpendicular to the direction of the detection signal emitted by the source module.

4. The optical sensor system according to claim 3, wherein each one of the source shielding member and the detection shielding member comprise:
an elongated body having a longitudinal opening extending throughout and open to an unsupported end of the elongated body.

5. The optical sensor system according to claim 4, wherein a shape of an outer surface of the respective elongated bodies surrounding the respective perimeters of the source window member and the detection window member are circular shaped.

6. The optical sensor system according to claim 4, wherein a shape of an outer surface of the respective elongated bodies surrounding the respective perimeters of the source window member and the detection window member are rectangular-shaped.

7. The optical sensor system according to claim 4, wherein a cross-sectional area of the longitudinal opening of the elongated body is greater than a cross-sectional area of the source window member and the detection window member perpendicular to a direction of the detection signal emitted by the source module.

8. The optical sensor system according to claim 1, wherein the detection module detects volatile organic compounds (VOC) present in the path of the detection signal between the source module and the detection module.

9. The optical sensor system according to claim 8, wherein the source shielding member reduces deposit formation of the VOC on the source window member and the detection shielding member reduces deposit formation of the VOC on the detection window member.

10. The optical sensor system according to claim 8, wherein the source shielding member and the detection shielding member extend substantially perpendicular to a direction of air flow transporting the VOC to block the air flow from directly contacting the source window member and the detection window member, respectively, in an uninterrupted manner.

11. An image forming apparatus, comprising:
a fluid applicator unit to apply fluid to an object to form an image; and
an optical sensor system to detect volatile organic compounds (VOC) formed from the fluid applied by the fluid applicator unit, the optical sensor system including a source module and a detection module spaced apart from each other;
the source module including a source housing unit having a source window member and a source shielding member, and to emit a detection signal through the source window member;
the source shielding member surrounding and extending in an outward direction from the source window member to reduce deposit formation of the VOC on the source window member;
the detection module including a detection housing unit having a detection window member and a detection shielding member, and to receive the detection signal emitted from the source module at the detection window member to detect the VOC present in a path of the detection signal between the source module and the detection module;
the detection shielding member surrounding and extending in an outward direction from the detection window member to reduce deposit formation of the VOC on the detection window member;
wherein the source shielding member and the detection shielding member are separate members with free ends thereof opposed to each other.

12. The image forming apparatus according to claim 11, wherein the optical sensor system further comprising:
at least one guide member to guide the source housing unit and the detection housing unit toward and away from each other to adjust a distance there between.

13. The image forming apparatus according to claim 11, wherein the source shielding member is concentric with and surrounds an entire perimeter of the source window member perpendicular to a direction of the detection signal emitted by the source module and the detection shielding member is concentric with and surrounds an entire perimeter of the detection window member perpendicular to the direction of the detection signal emitted by the source module.

14. The image forming apparatus according to claim 11, wherein each one of the source shielding member and the detection shielding member comprise:
an elongated body having a longitudinal opening extending throughout and open to an unsupported end of the elongated body.

15. The image forming apparatus according to claim 14, wherein a cross-sectional area of the longitudinal opening of the elongated body is greater than a cross-sectional area of the source window member and the detection window member perpendicular to a direction of the detection signal emitted by the source module.

16. The image forming apparatus according to claim 11, wherein the source shielding member and the detection shielding member extend substantially perpendicular to a direction of air flow transporting the VOC to block the air flow from directly contacting the source window member and the detection window member, respectively, in an uninterrupted manner.

17. The image forming apparatus according to claim 11, wherein the fluid comprises low weight liquid aliphatic hydrocarbon fluids.

18. A method of detecting volatile organic compounds, the method comprising:
emitting a detection signal by a source module through a source window member thereof;
receiving the detection signal by a detection module spaced apart from the source module through a detection window member thereof;
reducing deposit formation of the VOC on the source window member by a source shielding member of the source module surrounding and extending in an outward direction from the source window member with an open end of the source shielding member spaced from and opposed to the detection module;
reducing deposit formation of the VOC on the detection window member by a detection shielding member of the detection module surrounding and extending in an outward direction from the detection window member with an open end of the detection shielding member spaced from and opposed to the source module; and
detecting the volatile organic compounds present in a path of the detection signal between the source module and the detection module.

19. The method according to claim 18, wherein the reducing deposit formation of the VOC on the source window member and the detection window member further comprises:
blocking air flow transporting the VOC from directly contacting the source window member in an uninterrupted manner by an elongated body of the source shielding member disposed traverse to a direction of the air flow; and
blocking air flow transporting the VOC from directly contacting the detection window member in an uninterrupted manner by an elongated body of the detection shielding member disposed traverse to a direction of the air flow.

20. The method according to claim 18, wherein the reducing deposit formation of the VOC on the source window member and the detection window member further comprises:
  spacing and opposing the respective open ends of the source shielding member and the detection shielding member from and to each other.

\* \* \* \* \*